United States Patent
Eckl

(10) Patent No.: US 9,510,118 B2
(45) Date of Patent: Nov. 29, 2016

(54) MAPPING SYSTEM WITH MOBILE COMMUNICATION TERMINALS FOR MEASURING ENVIRONMENTAL SOUND

(71) Applicant: Roland Eckl, Forchheim (DE)

(72) Inventor: Roland Eckl, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/698,577

(22) Filed: Apr. 28, 2015

(65) Prior Publication Data

US 2015/0312689 A1 Oct. 29, 2015

(30) Foreign Application Priority Data

Apr. 29, 2014 (DE) .................. 10 2014 208 035

(51) Int. Cl.
| | |
|---|---|
| H03G 3/20 | (2006.01) |
| H04R 29/00 | (2006.01) |
| G01H 3/00 | (2006.01) |
| H04R 1/10 | (2006.01) |
| A61B 5/00 | (2006.01) |
| A61B 5/11 | (2006.01) |

(52) U.S. Cl.
CPC .............. *H04R 29/00* (2013.01); *G01H 3/00* (2013.01); *A61B 5/1112* (2013.01); *A61B 5/6803* (2013.01); *A61B 5/6898* (2013.01); *A61B 2560/0242* (2013.01); *H04R 1/1083* (2013.01); *H04R 2499/11* (2013.01)

(58) Field of Classification Search
CPC ........ H04R 27/00; H04R 29/00; H03G 3/24; H03G 3/32; H03G 9/005; H03G 9/025
See application file for complete search history.

(56) References Cited

U.S. PATENT DOCUMENTS

| | | | | |
|---|---|---|---|---|
| 8,555,721 B2* | 10/2013 | Taillet | ...................... | G01H 3/12 367/119 |
| 2009/0111486 A1* | 4/2009 | Burstrom | .......... | H04M 1/72547 455/456.3 |
| 2014/0067189 A1* | 3/2014 | Smith | .................... | G08G 1/166 701/29.1 |
| 2015/0172441 A1* | 6/2015 | Samhat | ............. | H04M 1/72563 455/418 |
| 2015/0271613 A1* | 9/2015 | Farahat | .................... | G01H 3/04 381/56 |

OTHER PUBLICATIONS

Canadian Centre for Occupational; Noise—Measurement of Workplace Noise; Canadian Centre for Occupational Health and Safety; Apr. 3, 2014.

(Continued)

*Primary Examiner* — Simon Sing
(74) *Attorney, Agent, or Firm* — Lempia Summerfield Katz LLC

(57) ABSTRACT

Environmental sound is captured and mapped. Application of a large number of mobile communication terminals embodied as a data supplier leads to extensive, automatic and continual mapping of environmental sound. For sites that are visited relatively frequently and by a plurality of subscribers, a relatively large quantity of remotely transmitted data records for the environmental sound is obtained informally, which permits a more precise depiction of the environmental noise. Commercially available mobile communication terminals may be augmented using simple measures in order to communicate with a central or local mapping system or mapping service directly or indirectly.

15 Claims, 1 Drawing Sheet

(56) References Cited

OTHER PUBLICATIONS

German Office Action for German Application No. 10 2014 208 035.5, mailed Feb. 10, 2015 with English Translation.

Ruge L. et al: SoundOfTheCity—Continuous Noise Monitoring for a Healthy City; 5th International Workshop on Smart Environments and Ambient Intelligence 2013, San Diego; IEEE 2013 International Conference; pp. 670-675; Mar. 22, 2013.

* cited by examiner

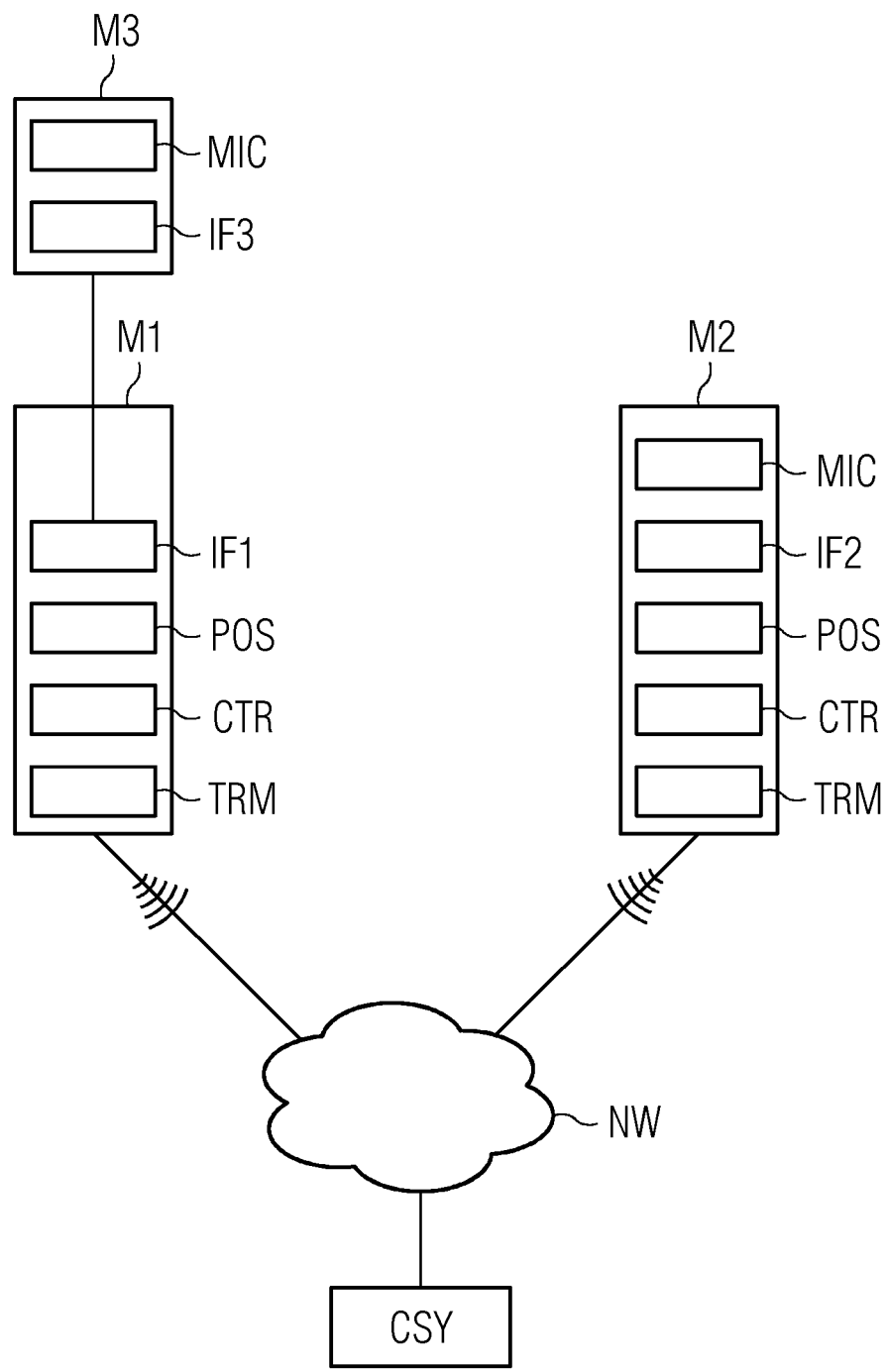

MAPPING SYSTEM WITH MOBILE COMMUNICATION TERMINALS FOR MEASURING ENVIRONMENTAL SOUND

CROSS-REFERENCE TO RELATED APPLICATIONS

The present patent document claims the benefit of DE 10 2014 208 035.5, filed on Apr. 29, 2014, which is hereby incorporated by reference.

TECHNICAL FIELD

The disclosed embodiments relate to a mapping system having mobile communication terminals for measuring environmental sound.

BACKGROUND

Environmental sound or environmental noise has a burdensome or harmful effect on human beings, depending on the sound level. Measures to avoid environmental noise are usually preceded by surveys that include mapping of noise pollution and computation of the number of human beings affected by environmental noise. Such mapping of the noise pollution is also advised in a European Guideline 2002/49/EG relating to the rating and tackling of environmental noise.

Capture and mapping of environmental sound in current practice is complex and effected only sporadically. Capture operations may be performed at fixed intervals of time (e.g., every 5 years), and are undertaken at representative places over a prescribed period. Instead of extensive measurement of environmental sound, computations or estimations are predominantly used. In this context, special sources of emission (e.g., traffic routes) are used and the effect thereof on the environment extrapolated (e.g., taking account of buildings and other obstacles). Such computation or estimation has numerous associated disadvantages. Among other things, by nature, such computation or estimation does not take account of frequenting of traffic routes depending on season or time of day.

At special sites (e.g., airports), continuous measurements are taken at static measuring devices, but these are likewise performed only at representative places on the airport premises.

Overall, such mapping of environmental sound is limited to a few measuring devices at discontinuous measurement times.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a system for measuring environmental sound that allows extensive and continuous capture of environmental sound levels at a respective geographical position for further processing in a mapping system is provided.

According to the disclosed embodiments, a mobile communication terminal for measuring environmental sound having an interface to an electroacoustic sound transducer for recording the environmental sound is provided. The electroacoustic sound transducer or microphone is either integrated in a commercially available mobile communication terminal or connected to the mobile communication terminal via an interface.

The communication terminal additionally includes a position finding unit for determining a position of the mobile communication terminal and for outputting a corresponding position datum. Position finding units in commercially available communication terminals provide for position finding based on global positioning system signals (GPS) and/or WLAN or Bluetooth signals using trilateration or fingerprinting methods to determine a geographical position.

According to the disclosed embodiments, a control unit that is configured to receive at least one recording of the environmental sound, to compute a sound level value for the recording and to create a data record is also provided. The data record includes at least one sound level value and a position datum at the time of the recording of the environmental sound.

In addition, the disclosed embodiments provide a transmission unit for remote transmission of the at least one data record. Remote transmission of the at least one data record may be effected via a wireless interface that is provided for conventional mobile communication terminals anyway.

The disclosed embodiments provide a mapping system including an interface to a plurality of mobile communication terminals and a processing unit for associating at least one remotely transmitted data record with geocoordinates on a digital map.

An advantage of the disclosed embodiments arises through application of mobile communication terminals embodied according to the disclosed embodiments as a data supplier for the creation of noise maps. Given a sufficient number of subscribers, extensive, automatic and continual noise mapping takes place. For sites that are visited relatively frequently and by a plurality of subscribers, a relatively large quantity of remotely transmitted data records for the environmental sound that permits a more precise depiction of the environmental noise is obtained informally.

Commercially available mobile communication terminals may be augmented according to the disclosed embodiments using simple measures in order to communicate with a central or local mapping system or mapping service directly or indirectly.

Advantageously, the customary measures for estimations or the creation of noise maps on a computational basis are unnecessary. According to the disclosed embodiments, it is possible to create maps based on actually occurring noise instead.

The advantageous realtime capability of the disclosed embodiments permits temporary events to be identified and recorded based on significant alterations in comparison with historic values.

A recording of the environmental sound is made from different geocoordinates based on the residence of a respective user of a mobile communication terminal. In a transparent environment, the remotely transmitted data records are therefore less susceptible to nonrepresentative recording positions owing to the scattered geocoordinates, and are therefore more precise.

The disclosed embodiments may be used to record environmental noise on a geographical basis. In addition, the individual noise pattern to which a single user is exposed may be ascertained. This embodiment permits conclusions to be drawn about the average noise exposure for the user (e.g., for medical purposes).

According to one embodiment, the data record to be transmitted additionally includes the time or the period of the recording of the environmental sound. This measure provides that the intensity of the environmental sound is represented based on the day and/or season or seasonally.

According to one embodiment, the data record to be transmitted additionally includes the frequency characteristics of the environmental sound. This measure provides more precise analysis of the type of the environmental sound. By way of example, based on a spectral distribution of the recorded environmental sound, it is possible to assess whether the environmental sound is industrial or road noise or whether the environmental sound is normal speech. Normal speech may be qualified as temporary environmental sound for noise mapping, which is disregarded.

According to one embodiment, the control unit is configured to evaluate the frequency characteristics of the environmental sound. According to this embodiment, the evaluation is taken as a basis for providing for the data record to be marked if the frequency characteristics of the environmental sound do not correspond to a type of the environmental sound that is envisaged for the transmission of the data record. Advantageously, the spectral distribution of the recorded environmental sound may thus be evaluated on the mobile communication terminal too, and data records that do not fit may be excluded from the transmission. Given a choice between the currently cited embodiment and the aforementioned embodiment, the advantages of reduced data transmission are to be weighted up against requirements for computation power on the mobile communication terminal.

According to one embodiment, the control unit is configured to evaluate data from a position sensor of the mobile communication terminal. If the present location of the mobile communication terminal does not correspond to a location that is envisaged for the transmission of the data record, the data record is marked accordingly, and transmission of the data record is abandoned. By way of example, transmission of the data record may be temporarily abandoned when the position sensor or the gyroscope of the mobile communication terminal delivers data that indicates that the mobile communication terminal would not deliver any useful data (e.g., because the mobile communication terminal is currently being carried in a trouser pocket).

According to one embodiment, the control unit is configured to evaluate a sound level value of the environmental sound. If the evaluated sound level value of the environmental sound does not correspond to a type of the environmental sound that is envisaged for the transmission of the data record, the data record is marked accordingly, and transmission of the data record is abandoned. Such a measure is useful particularly when a data record is not intended to be transmitted until a definable sound level is reached.

According to one embodiment, the interface to an electroacoustic sound transducer is set up for a communication link to a communication-terminal-external device that includes the electroacoustic sound transducer. By way of example, communication-terminal-external devices include headsets, hearing aids and all possible input and/or output appliances that may be connected to a mobile communication terminal and have an electroacoustic sound transducer (e.g., a microphone).

In an alternative embodiment, the communication-terminal-external device includes not only the electroacoustic sound transducer but also further functional units (e.g., the position finding unit).

BRIEF DESCRIPTION OF THE DRAWING

FIG. 1 depicts a schematic illustration of a plurality of mobile communication terminals and a mapping system.

DETAILED DESCRIPTION

FIG. 1 depicts a first mobile communication terminal M1 and a second mobile communication terminal M2 (e.g., two communication terminals) that are each connected to a data network NW via a communication link. The connection to the data network NW is of wireless design, at least in subsections.

The two mobile communication terminals M1, M2 have a respective transmission unit TRM, a respective control unit CTR, a respective position finding unit POS, and a respective interface IF1, IF2 to an electroacoustic sound transducer.

In the case of the second mobile communication terminal M2, a communication-terminal-internal electroacoustic sound transducer MIC is used. The communication-terminal-internal electroacoustic sound transducer MIC is a communication-terminal-internal microphone, for example. In the case of the first mobile communication terminal M1, a first interface IF1 to an electroacoustic sound transducer is provided. The first interface IF1 is operated to connect a communication-terminal-external device M3 via a third interface IF3 that is configured at that location.

Besides the third interface IF3, the communication-terminal-external device M3 has a dedicated electroacoustic sound transducer MIC that is configured to record the environmental sound. The communication-terminal-external device M3 is embodied as an input/output appliance that may be connected to the mobile communication terminal M1 via, for example, a wireless interface IF3. Examples of such communication-terminal-external devices M3 include headsets, hearing aids, etc.

The electroacoustic sound transducer MIC is used to record the environmental sound and to transfer the environmental sound to the control unit CTR. The control unit CTR computes a sound level value for the recording. The sound level value is inserted into a data record. Besides the sound level value, the data record also includes a position datum that characterizes the position of the mobile communication terminal M1, M2 at the time of the recording of the environmental sound. The position data is delivered by the position finding unit POS.

The respective transmission unit TRM is used to send the data record to a mapping system CSY via the data network NW. The mapping system CSY has an interface to a plurality of mobile communication terminals M1, M2 for receiving the data records sent. A processing unit (not shown)—of the mapping system associates the remotely transmitted data records with geocoordinates on a digital map.

In summary, the disclosed embodiments relate to capturing and mapping environmental sound. The application of a large number of mobile communication terminals embodied according to the disclosed embodiments as a data supplier leads to extensive, automatic and continual mapping of environmental sound. For sites that are visited relatively frequently and by a plurality of subscribers, a relatively large quantity of remotely transmitted data records for the environmental sound is obtained informally, which permits a more precise depiction of the environmental noise. Commercially available mobile communication terminals may be augmented according to the disclosed embodiments by using simple measures in order to communicate with a central or local mapping system or mapping service directly or indirectly.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A mobile communication terminal for measuring environmental sound, the mobile communication terminal comprising:
    an interface to an electroacoustic sound transducer for recording the environmental sound;
    a position finding unit configured to determine a position of the mobile communication terminal and to output a corresponding position datum;
    a control unit configured to:
        receive at least one recording of the environmental sound;
        compute a sound level value for the at least one recording;
        create a data record for the at least one recording, wherein the data record comprises at least one sound level value and a position datum at a time of the recording of the environmental sound;
        evaluate data from a position sensor of the mobile communication terminal; and
        mark the data record when a present location of the mobile communication terminal does not correspond to a location identified for transmission of the data record; and
    a transmission unit configured to remotely transmit the data record.

2. The mobile communication terminal of claim 1, wherein the data record further comprises the time or a time period of the recording of the environmental sound.

3. The mobile communication terminal of claim 1, wherein the data record further comprises frequency characteristics of the environmental sound.

4. The mobile communication terminal of claim 3, wherein the control unit is further configured to:
    evaluate the frequency characteristics of the environmental sound; and
    mark the data record when the frequency characteristics of the environmental sound do not correspond to a type of the environmental sound for the transmission of the data record.

5. The mobile communication terminal of claim 1, wherein the control unit is further configured to:
    evaluate the sound level value of the environmental sound; and
    mark the data record when the evaluated sound level value of the environmental sound does not correspond to a type of the environmental sound for the transmission of the data record.

6. The mobile communication terminal of claim 1, wherein the interface to the electroacoustic sound transducer is set up for a communication link to a communication-terminal-external device, the communication-terminal-external device comprising the electroacoustic sound transducer.

7. The mobile communication terminal of claim 2, wherein the data record further comprises frequency characteristics of the environmental sound.

8. The mobile communication terminal of claim 7, wherein the control unit is further configured to:
    evaluate the frequency characteristics of the environmental sound; and
    mark the data record when the frequency characteristics of the environmental sound do not correspond to a type of the environmental sound for the transmission of the data record.

9. A mobile communication terminal for measuring environmental sound, the mobile communication terminal comprising:
    an interface to an electroacoustic sound transducer for recording the environmental sound;
    a position finding unit configured to determine a position of the mobile communication terminal and to output a corresponding position datum;
    a control unit configured to:
        receive at least one recording of the environmental sound;
        compute a sound level value for the at least one recording;
        create a data record for the at least one recording, wherein the data record comprises at least one sound level value and a position datum at a time of the recording of the environmental sound, and frequency characteristics of the environmental sound;
        evaluate the frequency characteristics of the environmental sound;
        evaluate data from a position sensor of the mobile communication terminal;
        mark the data record when the frequency characteristics of the environmental sound do not correspond to a type of the environmental sound for transmission of the data record; and
        mark the data record when a present location of the mobile communication terminal does not correspond to a location identified for the transmission of the data record; and
    a transmission unit configured to remotely transmit the data record.

10. A mapping system comprising:
    an interface to a plurality of mobile communication terminals, a mobile communication terminal of the plurality of mobile communication terminals comprising:
        an interface to an electroacoustic sound transducer, wherein the electroacoustic sound transducer is configured to record an environmental sound;
        a position finding unit configured to determine a position of the mobile communication terminal and to output a corresponding position datum;
        a control unit configured to receive at least one recording of the environmental sound, to compute a sound level value for the at least one recording, to create a data record for the at least one recording, to evaluate data from a position sensor of the mobile communication terminal, and to mark the data record when a present location of the mobile communication terminal does not correspond to a location identified for transmission of the data record, wherein the data record comprises at least one sound level value and a position datum at a time of the recording of the environmental sound; and a transmission unit configured to remotely transmit the data record; and a processing unit configured to associate at least one remotely transmitted data record with geocoordinates on a digital map.

11. The mapping system of claim 10, wherein the data record further comprises the time or a time period of the recording of the environmental sound.

12. The mapping system of claim 10, wherein the data record further comprises frequency characteristics of the environmental sound.

13. The mapping system of claim 12, wherein the control unit is further configured to:

evaluate the frequency characteristics of the environmental sound; and mark the data record when the frequency characteristics of the environmental sound do not correspond to a type of the environmental sound for the transmission of the data record.

14. The mapping system of claim 10, wherein the control unit is further configured to:

evaluate the sound level value of the environmental sound; and mark the data record when the evaluated sound level value of the environmental sound does not correspond to a type of the environmental sound for the transmission of the data record.

15. The mapping system of claim 10, wherein the interface to the electroacoustic sound transducer is set up for a communication link to a communication-terminal-external device, the communication-terminal-external device comprising the electroacoustic sound transducer.

* * * * *